US008784783B2

(12) United States Patent
Bridgeman et al.

(10) Patent No.: US 8,784,783 B2
(45) Date of Patent: *Jul. 22, 2014

(54) METHODS AND MATERIALS FOR PROVIDING TEETH WITH A WHITE APPEARANCE

(71) Applicant: SafeWhite LLC, Worthington, OH (US)

(72) Inventors: Scott Joseph Bridgeman, Delaware, OH (US); Richard Simon Brody, Columbus, OH (US); Thomas Joel Zupancic, Powell, OH (US)

(73) Assignee: SafeWhite LLC, Worthington, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/029,115

(22) Filed: Sep. 17, 2013

(65) Prior Publication Data

US 2014/0010767 A1    Jan. 9, 2014

Related U.S. Application Data

(63) Continuation of application No. 13/216,757, filed on Aug. 24, 2011, now Pat. No. 8,568,698.

(60) Provisional application No. 61/376,523, filed on Aug. 24, 2010.

(51) Int. Cl.
*A61Q 11/00* (2006.01)
*A61K 8/64* (2006.01)

(52) U.S. Cl.
USPC ............ 424/49; 514/21.2; 514/775; 530/350; 530/360

(58) Field of Classification Search
CPC combination set(s) only.
See application file for complete search history.

(56) References Cited

U.S. PATENT DOCUMENTS

| | | | |
|---|---|---|---|
| 4,657,853 | A | 4/1987 | Freytag et al. |
| 4,713,254 | A | 12/1987 | Childs et al. |
| 5,391,497 | A | 2/1995 | Menon et al. |
| 5,834,427 | A | 11/1998 | Han et al. |
| 5,853,704 | A | 12/1998 | Zhang et al. |
| 5,876,995 | A | 3/1999 | Bryan |
| 6,080,844 | A | 6/2000 | Carney et al. |
| 6,113,886 | A | 9/2000 | Bryan |
| 6,121,421 | A | 9/2000 | Schwartz et al. |
| 6,506,577 | B1 | 1/2003 | Deming et al. |
| 6,558,717 | B1 | 5/2003 | Kollmann et al. |
| 6,780,844 | B1 | 8/2004 | Reynolds |
| 6,797,810 | B1 | 9/2004 | Savolainen |
| 7,166,424 | B2 | 1/2007 | Michnick et al. |
| 7,393,923 | B2 | 7/2008 | Tsien et al. |
| 7,666,996 | B2 | 2/2010 | Sidelman |
| 8,568,698 | B2 | 10/2013 | Bridgement et al. |
| 2004/0136926 | A1 | 7/2004 | Periathamby et al. |
| 2006/0034780 | A1 * | 2/2006 | Guan et al. ............ 424/49 |
| 2009/0074680 | A1 | 3/2009 | Anderson et al. |
| 2010/0062460 | A1 | 3/2010 | Pande et al. |
| 2010/0144598 | A1 | 6/2010 | Fine et al. |
| 2010/0203533 | A1 | 8/2010 | Desai et al. |
| 2010/0247457 | A1 | 9/2010 | Anton et al. |

FOREIGN PATENT DOCUMENTS

| | | |
|---|---|---|
| WO | WO 2004/035077 | 4/2004 |
| WO | WO 2006/100501 | 9/2006 |
| WO | WO 2006/135982 | 12/2006 |

OTHER PUBLICATIONS

Shaner et al. Advances in fluorescent protein technology. J Cell Sci. Dec. 15, 2007;120(Pt 24):4247-60.*
GC America Inc. MI Paste™ &MI Paste Plus™. 2008.*
Authorized Officer A. Evers. International Search Report and Written Opinion in International Application No. PCT/US2011/048976, dated Dec. 30, 2011, 12 pages.
International Preliminary Report on Patentability in International Application No. PCT/US2011/048976, mailed Feb. 26, 2013, 7 pages.
Australian Office Action in AU Application No. 2011293349, issued Oct. 21, 2013, 3 pages.
Alieva et al., "Diversity and Evolution of Coral Fluorescent Proteins," *PLoS ONE*, 2008, 3(7):1-12.
Anderson et al., "The Contribution of DOPA to Substrate-Peptide Adhesion and Internal Cohesion of Mussel-Inspired Synthetic Peptide Films," *Advanced Functional Materials*, 2010, 20:4196-4205.
Bouropoulos et al., "Analysis of hydroxyapatite surface coverage by amelogenin nanospheres following the Langmuir model for protein adsorption.," *Calcif. Tissue Int.*, 2003, 72:599-603.
Chudakov et al., "Fluorescent Proteins and Their Applications in Imaging Living Cells and Tissues," *Physiol. Rev.*, 2010, 90:1103-1163.
Dalsin, "Mussel Adhesive Protein Mimetic Polymers for the Preparation of Nonfouling Surfaces," *J. Am. Chem. Soc.*, 2003, 125:4253-4258.
Filpula et al., "Structural and Functional Repetition in a Marine Mussel Adhesive Protein," *Biotechnol. Prog.* 1900, 6:171-177.
Fuller et al., "DOPA-Containing Polypeptides I. Improved Synthesis of High-Molecular-Weight Poly(L-DOPA) and Water-Soluble Copolypeptides," *Biopolymers*, 1978, 17:2939-2943.
GenBank® Accession No. 2ZMW_D, May 2, 2012, 2 pages.
GenBank® Accession No. 3GEX_A, Mar. 10, 2010, 2 pages.
GenBank® Accession No. 3M24_A, May 26, 2010, 2 pages.
GenBank® Accession No. 3M24_B, May 26, 2010, 2 pages.
GenBank® Accession No. 3M24_C, May 26, 2010, 2 pages.
GenBank® Accession No. 3M24_D, May 26, 2010, 2 pages.
GenBank® Accession No. AAG16224.1, Sep. 26, 2000, 1 page.
GenBank® Accession No. AAU06852.1, Oct. 31, 2008, 1 page.
GenBank® Accession No. AAV52166.1, Dec. 17, 2004, 1 page.
GenBank® Accession No. AAV52170.1, Dec. 17, 2004, 1 page.

(Continued)

*Primary Examiner* — Karlheinz R Skowronek
*Assistant Examiner* — Jia-Hai Lee
(74) *Attorney, Agent, or Firm* — Fish & Richardson P.C.

(57) ABSTRACT

This document provides methods and materials for providing teeth with a white appearance. For example, methods and materials for contacting teeth with one or more fluorescence emitting polypeptides (e.g., a blue fluorescent protein (BFP)) to provide the teeth with a whiter appearance are provided.

8 Claims, 10 Drawing Sheets

(56) References Cited

OTHER PUBLICATIONS

GenBank® Accession No. AAV73970.1, Jul. 1, 2005, 1 page.
GenBank® Accession No. AB038175.1, Jan. 5, 2002, 2 pages.
GenBank® Accession No. ABM97856, Sep. 10, 2007, 1 page.
GenBank® Accession No. ABM97857, Sep. 10, 2007, 1 page.
GenBank® Accession No. ABN30727.1, Feb. 7, 2007, 1 page.
GenBank® Accession No. ABR26680.1, Jul. 27, 2007, 1 page.
GenBank® Accession No. ACF35425.1, Jul. 19, 2008, 1 page.
GenBank® Accession No. ACH06540.1, Aug. 18, 2008, 1 page.
GenBank® Accession No. ACH06541.1, Aug. 18, 2008, 1 page.
GenBank® Accession No. ACJ06700.1, Apr. 13, 2009, 1 page.
GenBank® Accession No. ACO48263.1, Jul. 8, 2009, 1 page.
GenBank® Accession No. ACO48275.1, Jul. 8, 2009, 1 page.
GenBank® Accession No. ACO48285.1, Jul. 8, 2009, 1 page.
GenBank® Accession No. ACQ43939.1, Nov. 1, 2009, 1 page.
GenBank® Accession No. ACU30027.1, Aug. 15, 2009, 1 page.
GenBank® Accession No. ACV20892.1, Sep. 1, 2009, 1 page.
GenBank® Accession No. ACY24904.1, Nov. 1, 2009, 1 page.
GenBank® Accession No. ADC42843.1, Feb. 9, 2010, 1 page.
GenBank® Accession No. ADD23343.1, Mar. 22, 2010, 1 page.
GenBank® Accession No. ADE48830.1, Apr. 10, 2010, 1 page.
GenBank® Accession No. ADE48834.1, Apr. 10, 2010, 1 page.
GenBank® Accession No. BAD52001.1, Sep. 29, 2004, 1 page.
GenBank® Accession No. BAE53441.1, Dec. 16, 2010, 1 page.
GenBank® Accession No. CAE00361.1, Jun. 25, 2003, 1 page.
GenBank® Accession No. CAE00365.1, Jun. 25, 2003, 1 page.
GenBank® Accession No. EDU39924.1, May 13, 2008, 2 pages.
GenBank® Accession No. EF517317, Jun. 14, 2007, 1 page.
GenBank® Accession No. EF517318, Jun. 14, 2007, 1 page.
GenBank® Accession No. U70495.1, Oct. 12, 1996, 1 page.
GenBank® Accession No. U70496.1, Oct. 12, 1996, 1 page.
GenBank® Accession No. U70497.1, Oct. 12, 1996, 1page.
GenBank® Accession No. U87625.1, Dec. 21, 1999, 1 page.
Hermanson. Part 1: Section 4, Part 2: Second Edition, 2008 Section 5, Part 2: section 25, *Bioconjugate Techniques, Second Edition*, 2008.
Hoshino, et al. "The Effect of Polymerization of Horseradish Peroxidase on the Peroxidase Activity in the Presence of Excess H2O2: A background for a Homogeneous Enzyme Immunoassay," *J. Biochem*, 1987, 102:785-791.
Hwang et al., "Expression of functional recombinant mussel adhesive protein Mgfp-5 in *Escherichiacoli*," *Environ. MicroBiol.*, 2004, 70:3352-3359.
Hwang et al., "Practical Recombinant 3568 Hybrid Mussel Bioadhesive," *Biomaterials*, 2007, 28:3560-3568.
Jain et al., "Purification of recombinant green fluorescent protein by three-phase partitioning," *J. Chromatography A*, 2004, 1035:83-86.
Kim et al., "Porous chitosan-based adhesive patch filled with poly(L-3,4-dihydroxyphenylalanine) as a transdermal drug-delivery system," *J. Porous Mater*, 2013, 20:177-182.
Kitamura et al., "Expression of a Model Peptide of a Marine Mussel Adhesive Protein in *Escherichia coli* and Characterization of its Structural and Functional Properties," J. *Polymer Science: Part A: Polymer Chemistry*, 1991, 37:729-736.
Lacy et al., "Free sulfhydryl measurement as an indicator of antibody stability," *Analytical Biochemistry*, 2008, 382:66-68.
Lamkin et al., "Temporal and compositional characteristics of salivary protein adsorption to hydroxyapatite," *J. Dent. Res.*, 1996, 75:803-808.
Laulicht, "Bioinspired Bioadhesive Polymers: Dopa-Modified Poly(acrylic acid) Derivatives," *Macromol. Biosci.*, 2012, 12:1555-1565.

Lee et al., "Facile Conjugation of Biomolecules onto Surfaces via Mussel Adhesive Protein Inspired Coatings," *Adv. Mater*, 2009, 21:431-434 (Author Manuscript).
Lee et al., "Mussel-inspired adhesives and coatings," *Annu. Rev. Mater. Res.*, 2011, 41:99-132.
Lee et al., "Single-molecule mechanics of mussel adhesion," PNAS, 2006, 103(35): 12999-13003.
Lewis, "Dual Detection of Peptides in a Fluorescence Binding Assay by Employing Genetically Fused GFP and BFP Mutants," *Anal. Chem.*, 1999, 71:4321-4327.
Lim et al, "The Adhesive Properties of Coacervated Recombinant Hybrid Mussel Adhesive Proteins," *Biomaterials*, 2010, 31: 3715-3722.
Lin et al., "Adhesion mechanisms of the mussel foot proteins mfp-1 and mfp-3," *PNAS*, 2007, 104 (10): 3782-3786.
McCall et al., "Simplified method for conjugating macrocyclic bifunctional chelating agents to antibodies via 2-iminothioane," *Bioconjugate Chem.*, 1990, 1(3):222-226.
Mena et al., "Blue fluo5rescent proteins with enhanced brightness and photosta-bility from a structurally targeted library," *Nature Biotechnology*, 2006, 24:1569-1571.
Paravina et al., "New shade guide for evaluation of tooth whitening—colorimetric study," *J. Esthet. Restor. Dent.*, 2007, 19:276-283.
Park et al., "Influence of fluorescent whitening agent on the fluorescent emission of resin composites," *Dental Materials*, 2007, 23:731-735.
Payne, "Polymerization of Proteins with Glutaraldehyde, Soluble molecular-weight markers" *Biochem J*, 1973, 135:867-873.
Raj et al., "Salivary Statherin: Dependence on Sequence, charge, Hydrogen Bonding Potency, and Helical conformation for Adsorption to Hydroxyapatite and Inhibition of Mineralization," *J. Biol. Chem.*, 1992, 267:5968-5976.
Reynolds et al., "A Selective Precipitation Purification Procedure for Multiple Phosphoseryl-Containing Peptides and Methods for Their Identification," *Anal. Biochem.*, 1994, 217:277-284.
Silverman and Roberto, "Understanding Marine Mussel Adhesion," Marine *BioTechnol*, 2007, 9:661-681.
Singh, "A Sensitive Assay for Maleimide Groups," *Bioconjugate Chem.*, 1994, 5:348-351.
Siqueira et al., "Small molecular weight proteins/peptides present in the in vivo formed human acquired enamel pellicle," *Archives of Oral Biology*, 2009, 54:437-444.
Slayton, "Molecular Recognition at the Protein-Hydroxyapatite Interface," *Critical Reviews in Oral Biology & Medicine*, 2003, 14(5):370-376.
Subach et al., "Conversion of Red Fluorescent Protein into a Bright Blue Probe," *Chemistry & Biology*, 2008, 15:1116-1124.
Wait, "Marine adhesive proteins: natural composite thermosets," *Int. J. Biol. Macromol*, 1990, 12:139-144.
Walker, "Increased remineralization of tooth enamel by milk containing added casein phosphopeptide-amorphous calcium phosphate," *J Diary Res.*, 2006, 73:74-78.
Yakhnin et al., "Green fluorescent protein purification by organic extraction," *Protein Expr. Purif.*, 1998, 14:382-386.
Yao, "Pellicle Precursor Proteins: Acidic Proline-rich Proteins, Statherin, and Histatins, and their Crosslinking Reaction by Oral Transglutaminase," *J Dental Res.*, 1999, 79(11):1696-1703.
Yu et al., Mussel protein adhesion depends on thiol-mediated redox modulation, *Nat Chem Biol.*; 2012, 7(9): 588-590 (Author Manuscript).

* cited by examiner

Figure 1

```
  1 ggatccaagg agatataaca atgagtaaag gagaagaact tttcactgga gttgtcccaa
 61 ttcttgttga attagatggt gatgttaatg ggcacaaatt ttctgtcagt ggagagggtg
121 aaggtgatgc aacatacgga aaacttaccc ttaaatttat ttgcactact ggaaaactac
181 ctgttccatg gccaacactt gtcactactt tctctcatgg tgttcaatgc ttttcaagat
241 acccagatca tatgaagcgg cacgacttct tcaagagcgc catgcctgag ggatacgtgc
301 aggagaggac catctctttc aaggacgacg gaactacaa gacacgtgct gaagtcaagt
361 ttgagggaga caccctcgtc aacaggatcg agcttaaggg aatcgatttc aaggaggacg
421 gaaacatcct cggccacaag ttggaataca actacaactc ccacaacgta tacatcacgg
481 cagacaaaca aaagaatgga atcaaagcta acttcaaaat tagacacaac attgaagatg
541 gaagcgttca actagcagac cattatcaac aaaatactcc aattggcgat ggccctgtcc
601 ttttaccaga caaccattac ctgtccacac aatctgccct ttcgaaagat cccaacgaaa
661 agagagacca catggtcctt cttgagtttg taacagctgc tgggattaca catggcatgg
721 atgaactata caaataagag ctc
```

Figure 2

```
  1 MSKGEELFTG VVPILVELDG DVNGHKFSVS GEGEGDATYG KLTLKFICTT GKLPVPWPTL
 61 VTTFSHGVQC FSRYPDHMKR HDFFKSAMPE GYVQERTISF KDDGNYKTRA EVKFEGDTLV
121 NRIELKGIDF KEDGNILGHK LEYNYNSHNV YITADKQKNG IKANFKIRHN IEDGSVQLAD
181 HYQQNTPIGD GPVLLPDNHY LSTQSALSKD PNEKRDHMVL LEFVTAAGIT HGMDELYK
```

Figure 3

```
   1 agtaggttta aatagcttgg aagcaaaagt ctgccatcac cttgatcatc aacccagctt
  61 gctgcttctt cccagtcttg ggttcaagat cttgacaacc atgaaacttc tcatccttac
 121 ctgtcttgtg gctgttgctc ttgctaggcc taaacatcct atcaagcacc aaggactccc
 181 tcaagaagtc ctcaatgaaa atttactcag gttttttgtg gcaccttttc cagaagtgtt
 241 tggaaaggag aaggtcaatg aactgagcaa ggatattggg agtgaatcaa ctgaggatca
 301 agccatggaa gatattaagc aaatggaagc tgaaagcatt tcgtcaagtg aggaaattgt
 361 tcccaatagt gttgagcaga agcacattca aaaggaagat gtgccctctg agcgttacct
 421 gggttatctg gaacagcttc tcagactgaa aaaatacaaa gtacccagc tggaaattgt
 481 tcccaatagt gctgaggaac gacttcacag tatgaaagag ggaatccatg cccaacagaa
 541 agaacctatg ataggagtga atcaggaact ggcctacttc taccctgagc ttttcagaca
 601 attctaccag ctggatgcct atccatctgg tgcctggtat tacgttccac taggcacaca
 661 atacactgat gccccatcat tctctgacat ccctaatcct attggctctg agaacagtga
 721 aaagactact atgccactgt ggtgaggagt caagtgaatt ctgagggact ccacagttat
 781 ggtctttgat ggttctgaaa attccatgct ctacatgtct tttcatctat catgtcaaac
 841 cattctatcc aaaggcttca actgctgttt tagaataggg caatctcaaa ttgaaggcac
 901 tctttcttct tgagttctct actgtatttt agatagtgta acatccttaa gtgaaattgt
 961 cctaacagct tgttacctaa attccagtag tatcatgctg gtataaaggc cactgagtca
1021 aagggattaa agtcttcatt aaatttctgt atggaaaatg ttttaaaagc ctttgaatca
1081 cttctcctgt aagtgccatc atatcaaata attgtgtgca ttaactgaga ttttgtcttt
1141 cttcttttca ataaattaca ttttaaggca ct
```

Figure 4

```
  1 MKLLILTCLV AVALARPKHP IKHQGLPQEV LNENLLRFFV APFPEVFGKE KVNELSKDIG
 61 SESTEDQAME DIKQMEAESI SSSEEIVPNS VEQKHIQKED VPSERYLGYL EQLLRLKKYK
121 VPQLEIVPNS AEERLHSMKE GIHAQQKEPM IGVNQELAYF YPELFRQFYQ LDAYPSGAWY
181 YVPLGTQYTD APSFSDIPNP IGSENSEKTT MPLW
```

Figure 5

```
   1 tgatccattc agctcctcct tcacttcttg tcctctactt tggaaaaaag gaattgagag
  61 ccatgaaggt cctcatcctt gcctgcctgg tggctctggc ccttgcaaga gagctggaag
 121 aactcaatgt acctggtgag attgtggaaa gcctttcaag cagtgaggaa tctattacac
 181 gcatcaataa gaaaattgag aagtttcaga gtgaggaaca gcagcaaaca gaggatgaac
 241 tccaggataa aatccacccc tttgcccaga cacagtctct agtctatccc ttccctgggc
 301 ccatccataa cagcctccca caaaacatcc ctcctcttac tcaaacccct gtggtggtgc
 361 cgccttt cct tcagcctgaa gtaatgggag tctccaaagt gaaggaggct atggctccta
 421 agcacaaaga aatgcccttc cctaaatatc cagttgagcc ctttactgaa aggcagagcc
 481 tgactctcac tgatgttgaa aatctgcacc ttcctctgcc tctgctccag tcttggatgc
 541 accagcctca ccagcctctt cctccaactg tcatgtttcc tcctcagtcc gtgctgtccc
 601 tttctcagtc caaagtcctg cctgttcccc agaaagcagt gccctatccc cagagagata
 661 tgcccattca ggcctttctg ctgtaccagg agcctgtact cggtcctgtc cggggaccct
 721 tccctattat tgtctaagag gatttcaaag tgaatgcccc ctcctcactt ttgaattgac
 781 tgcgactgga aatatggcaa cttttcaatc cttgcatcat gttactaaga taattttta a
 841 atgagtatac atggaacaaa aaatgaaact ttattccttt atttatttta tgcttttt ca
 901 tcttaatttg aatttgagtc ataaactata tatttcaaaa ttttaattca acattagcat
 961 aaaagttcaa ttttaacttg gaaatatcat gaacatatca aaatatgtat aaaaataatt
1021 tctggaattg tgattattat ttctttaaga atctatttcc taaccagtca tttcaataaa
1081 ttaatcctta ggcaaaaaaa aaaaaaaa
```

Figure 6

```
  1 MKVLILACLV ALALARELEE LNVPGEIVES LSSSEESITR INKKIEKFQS EEQQQTEDEL
 61 QDKIHPFAQT QSLVYPFPGP IHNSLPQNIP PLTQTPVVVP PFLQPEVMGV SKVKEAMAPK
121 HKEMPFPKYP VEPFTERQSL TLTDVENLHL PLPLLQSWMH QPHQPLPPTV MFPPQSVLSL
181 SQSKVLPVPQ KAVPYPQRDM PIQAFLLYQE PVLGPVRGPF PIIV
```

Figure 7

```
  1 agggatctct tgaagcttca cttcaacttc actacttctg tagtctcatc ttgagtaaaa
 61 gagaacccag ccaactatga agttccttgt ctttgccttc atcttggctc tcatggtttc
121 catgattgga gctgattcat ctgaagagaa atttttgcgt agaattggaa gattcggtta
181 tgggtatggc ccttatcagc cagttccaga acaaccacta tacccacaac cataccaacc
241 acaataccaa caatatacct tttaatatca tcagtaactg caggacatga ttattgaggc
301 ttgattggca aatacgactt ctacatccat attctcatct ttcataccat atcacactac
361 taccactttt tgaagaatca tcaaagagca atgcaaatga aaaacactat aatttactgt
421 atactctttg tttcaggata cttgcctttt caattgtcac ttgatgatat aattgcaatt
481 taaactgtta agctgtgttc agtactgttt ctgaataata gaaatcactt ctctaaaagc
541 aataaatttc aagcacattt tcaaaaaaaa aaaaaaaaaa aaaaaaa
```

Figure 8

```
 1 mkflvfafil almvsmigad sseekflrri grfgygygpy qpvpeqplyp qpyqpqyqqy
61 tf
```

Figure 9

MSEELIKENMHMKLYMEGTVDNHHFKCTSEGEGKPYEGTQTMRIKVVEGGPLPFAFDI
LATSFLYGSKTFINHTQGIPDFFKQSFPEGFTWERVTTYEDGGVLTATQDTSLQDGCLIY
NVKIRGVNFTSNGPVMQKKTLGWEAFTETLYPADGGLEGRNDMALKLVGGSHLIANIK
TTYRSKKPAKNLKMPGVYYVDYRLERIKEANNETYVEQHEVAVARYCDLPSKLGHKL
N

SEQUENCE LISTING

```
<160> NUMBER OF SEQ ID NOS: 9

<210> SEQ ID NO 1
<211> LENGTH: 743
<212> TYPE: DNA
<213> ORGANISM: Artificial Sequence
<220> FEATURE:
<223> OTHER INFORMATION: Soluble-modified blue fluorescent protein

<400> SEQUENCE: 1
ggatccaagg agatataaca atgagtaaag gagaagaact tttcactgga gttgtcccaa      60
ttcttgttga attagatggt gatgttaatg ggcacaaatt ttctgtcagt ggagagggtg     120
aaggtgatgc aacatacgga aaacttaccc ttaaatttat ttgcactact ggaaaactac     180
ctgttccatg gccaacactt gtcactactt tctctcatgg tgttcaatgc ttttcaagat     240
acccagatca tatgaagcgg cacgacttct tcaagagcgc catgcctgag ggatacgtgc     300
aggagaggac catctctttc aaggacgacg ggaactacaa gacacgtgct gaagtcaagt     360
```

```
ttgagggaga caccctcgtc aacaggatcg agcttaaggg aatcgatttc aaggaggacg    420
gaaacatcct cggccacaag ttggaataca actacaactc ccacaacgta tacatcacgg    480
cagacaaaca aaagaatgga atcaaagcta acttcaaaat tagacacaac attgaagatg    540
gaagcgttca actagcagac cattatcaac aaaatactcc aattggcgat ggccctgtcc    600
ttttaccaga caaccattac ctgtccacac aatctgccct ttcgaaagat cccaacgaaa    660
agagagacca catggtcctt cttgagtttg taacagctgc tgggattaca catggcatgg    720
atgaactata caaataagag ctc                                           743
```

<210> SEQ ID NO 2
<211> LENGTH: 238
<212> TYPE: PRT
<213> ORGANISM: Artificial Sequence
<220> FEATURE:
<223> OTHER INFORMATION: Soluble-modified blue fluorescent protein

<400> SEQUENCE: 2

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser His Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 3
<211> LENGTH: 1172
<212> TYPE: DNA
<213> ORGANISM: Bos taurus

<400> SEQUENCE: 3

```
agtaggttta aatagcttgg aagcaaaagt ctgccatcac cttgatcatc aacccagctt     60
```

```
gctgcttctt cccagtcttg ggttcaagat cttgacaacc atgaaacttc tcatccttac    120
ctgtcttgtg gctgttgctc ttgctaggcc taaacatcct atcaagcacc aaggactccc    180
tcaagaagtc ctcaatgaaa atttactcag gttttttgtg gcacctttc cagaagtgtt    240 tggaaaggag aaggtcaatg aactgagcaa ggatattggg agtgaatcaa ctgaggatca    300
agccatggaa gatattaagc aaatggaagc tgaaagcatt tcgtcaagtg aggaaattgt    360
tcccaatagt gttgagcaga agcacattca aaggaagat gtgccctctg agcgttacct    420
gggttatctg gaacagcttc tcagactgaa aaatacaaa gtaccccagc tggaaattgt    480
tcccaatagt gctgaggaac gacttcacag tatgaaagag ggaatccatg cccaacagaa    540
agaacctatg ataggagtga atcaggaact ggcctacttc taccctgagc ttttcagaca    600
attctaccag ctggatgcct atccatctgg tgcctggtat tacgttccac taggcacaca    660
atacactgat gccccatcat tctctgacat ccctaatcct attggctctg agaacagtga    720
aaagactact atgccactgt ggtgaggagt caagtgaatt ctgagggact ccacagttat    780
ggtctttgat ggttctgaaa attccatgct ctacatgtct tttcatctat catgtcaaac    840
cattctatcc aaaggcttca actgctgttt tagaataggg caatctcaaa ttgaaggcac    900
tctttcttct tgagttctct actgtatttt agatagtgta acatccttaa gtgaaattgt    960
cctaacagct tgttacctaa attccagtag tatcatgctg gtataaaggc cactgagtca   1020
aagggattaa agtcttcatt aaatttctgt atggaaaatg ttttaaaagc ctttgaatca   1080
cttctcctgt aagtgccatc atatcaaata attgtgtgca ttaactgaga ttttgtcttt   1140
cttcttttca ataaattaca ttttaaggca ct                                 1172
```

<210> SEQ ID NO 4
<211> LENGTH: 214
<212> TYPE: PRT
<213> ORGANISM: Bos taurus

<400> SEQUENCE: 4

```
Met Lys Leu Leu Ile Leu Thr Cys Leu Val Ala Val Ala Leu Ala Arg
 1               5                  10                  15

Pro Lys His Pro Ile Lys His Gln Gly Leu Pro Gln Glu Val Leu Asn
             20                  25                  30

Glu Asn Leu Leu Arg Phe Phe Val Ala Pro Phe Pro Glu Val Phe Gly
         35                  40                  45

Lys Glu Lys Val Asn Glu Leu Ser Lys Asp Ile Gly Ser Glu Ser Thr
     50                  55                  60

Glu Asp Gln Ala Met Glu Asp Ile Lys Gln Met Glu Ala Glu Ser Ile
 65                  70                  75                  80

Ser Ser Ser Glu Glu Ile Val Pro Asn Ser Val Glu Gln Lys His Ile
                 85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
        115                 120                 125

Asn Ser Ala Glu Glu Arg Leu His Ser Met Lys Glu Gly Ile His Ala
    130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175
```

```
Gly Ala Trp Tyr Tyr Val Pro Leu Gly Thr Gln Tyr Thr Asp Ala Pro
                180                 185                 190

Ser Phe Ser Asp Ile Pro Asn Pro Ile Gly Ser Glu Asn Ser Glu Lys
            195                 200                 205

Thr Thr Met Pro Leu Trp
    210

<210> SEQ ID NO 5
<211> LENGTH: 1108
<212> TYPE: DNA
<213> ORGANISM: Bos taurus

<400> SEQUENCE: 5
tgatccattc agctcctcct tcacttcttg tcctctactt tggaaaaaag gaattgagag      60
ccatgaaggt cctcatcctt gcctgcctgg tggctctggc ccttgcaaga gagctggaag     120
aactcaatgt acctggtgag attgtggaaa gcctttcaag cagtgaggaa tctattacac     180
gcatcaataa gaaaattgag aagtttcaga gtgaggaaca gcagcaaaca gaggatgaac     240
tccaggataa aatccacccc tttgcccaga cacagtctct agtctatccc ttccctgggc     300
ccatccataa cagcctccca caaaacatcc ctcctcttac tcaaacccct gtggtggtgc     360
cgcctttcct tcagcctgaa gtaatgggag tctccaaagt gaaggaggct atggctccta     420
agcacaaaga aatgcccttc cctaaatatc cagttgagcc ctttactgaa aggcagagcc     480
tgactctcac tgatgttgaa aatctgcacc ttcctctgcc tctgctccag tcttggatgc     540
accagcctca ccagctcttc ctccaactgt catgtttcc tcctcagtcc gtgctgtccc      600
tttctcagtc caaagtcctg cctgttcccc agaaagcagt gccctatccc cagagagata     660
tgcccattca ggccttttctg ctgtaccagg agcctgtact cggtcctgtc cggggaccct     720
tccctattat tgtctaagag gatttcaaag tgaatgcccc ctcctcactt ttgaattgac     780
tgcgactgga aatatggcaa cttttcaatc cttgcatcat gttactaaga taattttttaa    840 atgagtatac atggaacaaa aaatgaaact ttattccttt atttatttta tgcttttttca    900 tcttaatttg aatttgagtc ataaactata tatttcaaaa ttttaattca acattagcat     960
aaaagttcaa ttttaacttg gaaatatcat gaacatatca aatatgtat aaaaataatt     1020 tctggaattg tgattattat ttctttaaga atctatttcc taaccagtca tttcaataaa    1080
ttaatcctta ggcaaaaaaa aaaaaaaa                                       1108

<210> SEQ ID NO 6
<211> LENGTH: 224
<212> TYPE: PRT
<213> ORGANISM: Bos taurus

<400> SEQUENCE: 6

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Thr Glu Asp Glu Leu Gln Asp Lys Ile
    50                  55                  60

His Pro Phe Ala Gln Thr Gln Ser Leu Val Tyr Pro Phe Pro Gly Pro
65                  70                  75                  80
```

```
Ile His Asn Ser Leu Pro Gln Asn Ile Pro Pro Leu Thr Gln Thr Pro
                 85                  90                  95
Val Val Val Pro Pro Phe Leu Gln Pro Glu Val Met Gly Val Ser Lys
            100                 105                 110
Val Lys Glu Ala Met Ala Pro Lys His Lys Glu Met Pro Phe Pro Lys
        115                 120                 125
Tyr Pro Val Glu Pro Phe Thr Glu Arg Gln Ser Leu Thr Leu Thr Asp
    130                 135                 140
Val Glu Asn Leu His Leu Pro Leu Pro Leu Leu Gln Ser Trp Met His
145                 150                 155                 160
Gln Pro His Gln Pro Leu Pro Thr Val Met Phe Pro Pro Gln Ser
                165                 170                 175
Val Leu Ser Leu Ser Gln Ser Lys Val Leu Pro Val Pro Gln Lys Ala
            180                 185                 190
Val Pro Tyr Pro Gln Arg Asp Met Pro Ile Gln Ala Phe Leu Leu Tyr
        195                 200                 205
Gln Glu Pro Val Leu Gly Pro Val Arg Gly Pro Phe Pro Ile Ile Val
    210                 215                 220

<210> SEQ ID NO 7
<211> LENGTH: 587
<212> TYPE: DNA
<213> ORGANISM: Homo sapiens

<400> SEQUENCE: 7
agggatctct tgaagcttca cttcaacttc actacttctg tagtctcatc ttgagtaaaa       60
gagaacccag ccaactatga agttccttgt ctttgccttc atcttggctc tcatggtttc     120
catgattgga gctgattcat ctgaagagaa attttttgcgt agaattggaa gattcggtta    180
tgggtatggc ccttatcagc cagttccaga caaccacta tacccacaac cataccaacc     240
acaataccaa caatatacct tttaatatca tcagtaactg caggacatga ttattgaggc     300
ttgattggca aatacgactt ctacatccat attctcatct tcataccat atcacactac      360 taccactttt tgaagaatca tcaaagagca atgcaaatga aaaacactat aatttactgt     420
atactctttg tttcaggata cttgccttt caattgtcac ttgatgatat aattgcaatt      480
taaactgtta agctgtgttc agtactgttt ctgaataata gaaatcactt ctctaaaagc     540
aataaatttc aagcacattt tcaaaaaaaa aaaaaaaaa aaaaaaa                   587

<210> SEQ ID NO 8
<211> LENGTH: 62
<212> TYPE: PRT
<213> ORGANISM: Homo sapiens

<400> SEQUENCE: 8

Met Lys Phe Leu Val Phe Ala Phe Ile Leu Ala Leu Met Val Ser Met
1               5                   10                  15
Ile Gly Ala Asp Ser Ser Glu Glu Lys Phe Leu Arg Arg Ile Gly Arg
            20                  25                  30
Phe Gly Tyr Gly Tyr Gly Pro Tyr Gln Pro Val Pro Glu Gln Pro Leu
        35                  40                  45
Tyr Pro Gln Pro Tyr Gln Pro Gln Tyr Gln Gln Tyr Thr Phe
    50                  55                  60

<210> SEQ ID NO 9
<211> LENGTH: 234
<212> TYPE: PRT
```

-continued

```
<213> ORGANISM: Artificial Sequence
<220> FEATURE:
<223> OTHER INFORMATION: mTagBFP Fluorescent Protein

<400> SEQUENCE: 9

Met Ser Glu Glu Leu Ile Lys Glu Asn Met His Met Lys Leu Tyr Met
1               5                   10                  15

Glu Gly Thr Val Asp Asn His His Phe Lys Cys Thr Ser Glu Gly Glu
                20                  25                  30

Gly Lys Pro Tyr Glu Gly Thr Gln Thr Met Arg Ile Lys Val Val Glu
            35                  40                  45

Gly Gly Pro Leu Pro Phe Ala Phe Asp Ile Leu Ala Thr Ser Phe Leu
        50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
                100                 105                 110

Asp Gly Cys Leu Ile Tyr Asn Val Lys Ile Arg Gly Val Asn Phe Thr
            115                 120                 125

Ser Asn Gly Pro Val Met Gln Lys Lys Thr Leu Gly Trp Glu Ala Phe
    130                 135                 140

Thr Glu Thr Leu Tyr Pro Ala Asp Gly Gly Leu Glu Gly Arg Asn Asp
145                 150                 155                 160

Met Ala Leu Lys Leu Val Gly Gly Ser His Leu Ile Ala Asn Ile Lys
                165                 170                 175

Thr Thr Tyr Arg Ser Lys Lys Pro Ala Lys Asn Leu Lys Met Pro Gly
            180                 185                 190

Val Tyr Tyr Val Asp Tyr Arg Leu Glu Arg Ile Lys Glu Ala Asn Asn
        195                 200                 205

Glu Thr Tyr Val Glu Gln His Glu Val Ala Val Ala Arg Tyr Cys Asp
    210                 215                 220

Leu Pro Ser Lys Leu Gly His Lys Leu Asn
225                 230
```

METHODS AND MATERIALS FOR PROVIDING TEETH WITH A WHITE APPEARANCE

CROSS-REFERENCE TO RELATED APPLICATION

This application is a continuation of U.S. application Ser. No. 13/216,757, filed Aug. 24, 2011, which claims the benefit of U.S. Provisional Application Ser. No. 61/376,523, filed Aug. 24, 2010. The disclosures of the prior application is considered part of (and is incorporated by reference in) the disclosure of this application.

BACKGROUND

1. Technical Field

This document relates to methods and materials involved in providing teeth with a white appearance. For example, this document relates to methods and materials for contacting teeth with one or more fluorescence emitting polypeptides (e.g., a blue fluorescent protein) to provide the teeth with a whiter appearance.

2. Background Information

In general, white teeth are considered cosmetically desirable. Teeth, however, can become discolored in the absence of intervention. The tooth structure that is generally responsible for presenting a stained appearance is the enamel layer. Several factors can contribute to enamel discoloration. For example, the formation of plaque and tartar matrices on the tooth surface can entrap stains, thereby leading to enamel discoloration.

Over-the-counter tooth whitening preparations have been developed to address the cosmetic preference of many to restore luster to tooth enamel discolored by surface entrapped materials. While all dentifrices and mouthwashes contain some cleaning and polishing agents, some enamel deposits become intractable to being fully removed by these agents under normal use conditions. Smokers often develop discolored enamel because the tars and particulates in exhaled cigarette smoke collect on the teeth. In some case, foods and drinks (e.g., tea) can stain or discolor tooth enamel.

SUMMARY

This document provides methods and materials for providing teeth with a white appearance. For example, this document provides methods and materials for contacting teeth with one or more fluorescence emitting polypeptides (e.g., a blue fluorescent protein (BFP)) to provide the teeth with a whiter appearance. As described herein, fluorescence emitting polypeptides such as BFP polypeptides can be applied to teeth under conditions that allow the fluorescence emitting polypeptides to attach or adhere directly or indirectly to the teeth. In such cases, the fluorescence emitting polypeptides can emit fluorescence at a particular wavelength. In the case of BFP polypeptides, the BFP polypeptides can emit fluorescence in the range of about 440 nm to about 500 nm (e.g., between about 450 nm and about 490 nm), which when emitted from teeth give the teeth a white appearance. This white appearance can occur even when the underlying teeth are not naturally that white. For example, the methods and materials provided herein can allow a person to have white appearing teeth even though the teeth may be stained. Thus, white appearing teeth can be obtained using the methods and materials provided herein without harsh bleaching (e.g., without dental bleaching treatments such as those involving hydrogen peroxide or carbimide peroxide) or de-staining techniques.

In general, one aspect of this document features a method for altering the appearance of teeth. The method comprises, or consists essentially of, applying a fluorescence emitting polypeptide to teeth, wherein fluorescence emitted from the fluorescence emitting polypeptide alters the appearance of the teeth. The teeth can be human teeth. The method can comprise altering the appearance of the teeth such that the teeth appear whiter. The fluorescence emitting polypeptide can be a BFP polypeptide. The fluorescence emitting polypeptide can be conjugated to a molecule having the ability to interact with or bind to a tooth or a tooth component. The molecule can be a polypeptide. The molecule can be a casein polypeptide. The molecule can be a statherin polypeptide. The molecule can be a molecule having the ability to interact with or bind to enamel, hydroxyapatite, or acquired dental pellicle. The fluorescence emitting polypeptide can be a fusion polypeptide comprising an amino acid sequence of a casein polypeptide. The fluorescence emitting polypeptide can be a fusion polypeptide comprising an amino acid sequence of a statherin polypeptide. The fluorescence emitting polypeptide can be present within tooth paste, and the applying step can comprise applying the tooth paste to the teeth. The fluorescence emitting polypeptide can be one unit of a polymer comprising two or more fluorescence emitting polypeptides. The polymer can be attached to a casein polypeptide to form a complex, wherein the complex is applied to the teeth.

In another aspect, this document features a composition comprising, or consisting essentially of, a fluorescence emitting polypeptide and a casein polypeptide.

In another aspect, this document features a composition comprising, or consisting essentially of, a fluorescence emitting polypeptide and a statherin polypeptide.

In another aspect, this document features a chimeric polypeptide comprising, or consisting essentially of, an amino acid sequence of 20 or more residues in length of a fluorescence emitting polypeptide and an amino acid sequence of 20 or more residues in length of a casein polypeptide. The chimeric polypeptide can comprise a full length fluorescence emitting polypeptide or fragment thereof that is at least about 90 percent identical to the full length fluorescence emitting polypeptide. The chimeric polypeptide can comprise a full length casein polypeptide or fragment thereof that is at least about 80 percent identical to the full length casein polypeptide. The chimeric polypeptide can comprise the ability to emit fluorescence and the ability to interact with or bind to a tooth or a tooth component.

In another aspect, this document features a chimeric polypeptide comprising, or consisting essentially of, an amino acid sequence of 20 or more residues in length of a fluorescence emitting polypeptide and an amino acid sequence of 20 or more residues in length of a statherin polypeptide. The chimeric polypeptide can comprise a full length fluorescence emitting polypeptide or fragment thereof that is at least about 90 percent identical to the full length fluorescence emitting polypeptide. The chimeric polypeptide can comprise a full length statherin polypeptide or fragment thereof that is at least about 80 percent identical to the full length statherin polypeptide. The chimeric polypeptide can comprise the ability to emit fluorescence and the ability to interact with or bind to a tooth or a tooth component.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a listing of a nucleic acid sequence (SEQ ID NO:1) that encodes an exemplary BFP polypeptide (GenBank Accession No. U70497.1; GI No. 1619752).

FIG. 2 is a listing of an amino acid sequence (SEQ ID NO:2) of an exemplary BFP polypeptide (GenBank Accession No. AAB16959.1; GI No. 1619753).

FIG. 3 is a listing of a nucleic acid sequence (SEQ ID NO:3) that encodes an exemplary α-casein polypeptide (GenBank Accession No. NM_181029.2; GI No. 31341348).

FIG. 4 is a listing of an amino acid sequence (SEQ ID NO:4) of an exemplary α-casein polypeptide (GenBank Accession No. NP_851372.1; GI No. 30794348).

FIG. 5 is a listing of a nucleic acid sequence (SEQ ID NO:5) that encodes an exemplary β-casein polypeptide (GenBank Accession No. BC111172.1; GI No. 83406092).

FIG. 6 is a listing of an amino acid sequence (SEQ ID NO:6) of an exemplary β-casein polypeptide (GenBank Accession No. AAI11173.1; GI No. 83406093).

FIG. 7 is a listing of a nucleic acid sequence (SEQ ID NO:7) that encodes an exemplary statherin polypeptide (GenBank Accession No. AAH67219.1; GI No. 45501309).

FIG. 8 is a listing of an amino acid sequence (SEQ ID NO:8) of an exemplary statherin polypeptide (GenBank Accession No. BC067219.1; GI No. 45501308).

FIG. 9 is a listing of an amino acid sequence (SEQ ID NO:9) of an exemplary BFP polypeptide.

DETAILED DESCRIPTION

Figure 10:
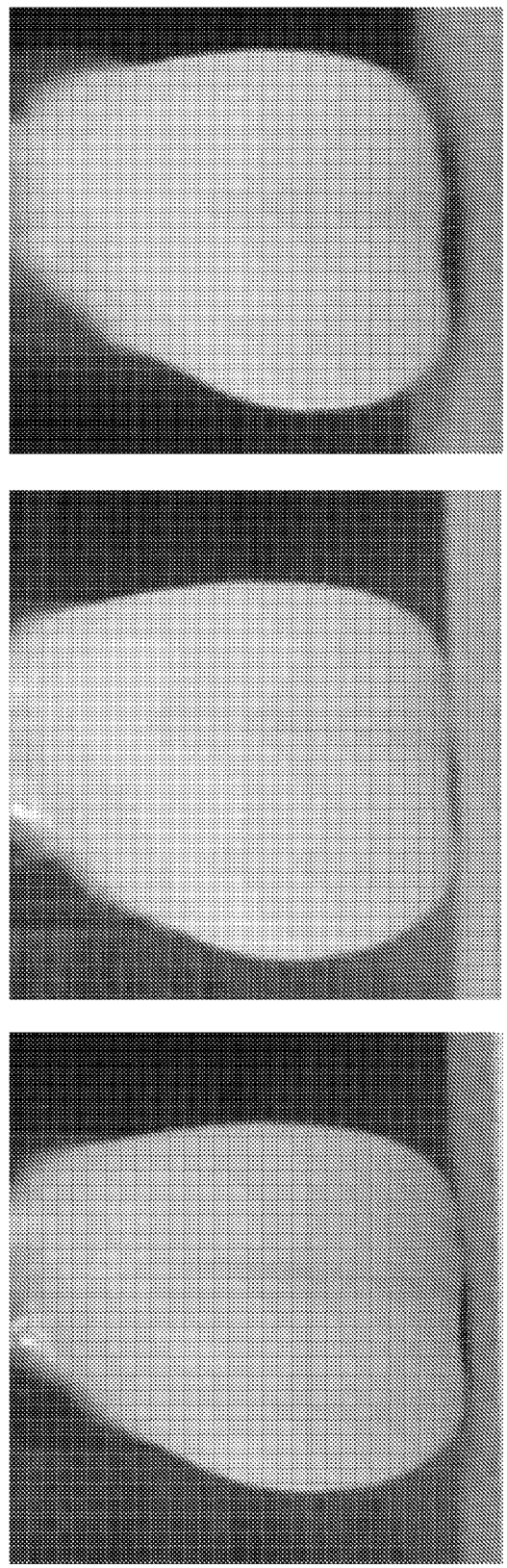
FIG. 10 contains photographs of a tooth at start (left), after applying a β-casein/BFP polypeptide conjugate (center), and after pumicing (right). The tooth exhibited a whiter appearance after applying a β-casein/BFP polypeptide conjugate than it did at start. This whiter appearance was lost after pumicing.

This document provides methods and materials for providing teeth with a white appearance. For example, this document provides methods and materials for contacting teeth with one or more fluorescence emitting polypeptides (e.g., a blue fluorescent protein (BFP)) to provide the teeth with a whiter appearance.

As described herein, fluorescence emitting polypeptides can be applied to teeth such that fluorescence is emitted from the teeth. Any appropriate fluorescence emitting polypeptide can be applied to teeth. For example, when the desire is to have whiter appearing teeth, a polypeptide that emits blue fluorescence can be applied to a person's teeth. Such blue fluorescence can have an emission wavelength between about 440 nm and about 500 nm (e.g., between about 450 nm and about 500 nm, between about 460 nm and about 500 nm, between about 470 nm and about 500 nm, between about 480 nm and about 500 nm, between about 440 nm and about 490 nm, between about 440 nm and about 480 nm, between about 440 nm and about 470 nm, between about 440 nm and about 460 nm, between about 450 nm and about 490 nm, or between about 460 nm and about 480 nm). In some cases, a fluorescence emitting polypeptide that emits fluorescence at an emission wavelength of between about 420 nm and about 450 nm, between about 430 nm and about 450 nm, between about 440 nm and about 450 nm, between about 420 nm and about 440 nm, or between about 485 nm and about 505 nm can be applied to teeth as described herein.

When the desire is to have teeth of a different color, a polypeptide that emits fluorescence in the red, green, or yellow spectrum can be applied to the person's teeth. Red fluorescence can have an emission wavelength between about 555 nm and about 655 nm (e.g., between about 565 nm and about 645 nm, between about 575 nm and about 635 nm, or between about 585 nm and about 625 nm). Green fluorescence can have an emission wavelength between about 500 nm and about 525 nm (e.g., between about 505 nm and about 520 nm or between about 510 nm and about 515 nm). Yellow fluorescence can have a wavelength between about 525 nm and about 555 nm (e.g., between about 530 nm and about 550 nm or 535 nm and about 545 nm). In some cases, a combination of different fluorescence emitting polypeptides can be applied to a person's teeth. For example, a combination of BFP polypeptides and red fluorescent protein (RFP) polypeptides can be applied to a person's teeth. In some cases, a combination of RFP polypeptides and green fluorescent protein (GFP) polypeptides can be applied to a person's teeth.

Any appropriate BFP polypeptide can be used as described herein. Examples of BFP polypeptides that can be used as described herein include, without limitation, EBFP (e.g., an EBFP having an emission max of 460 nm), fluorescent protein SBFP1 (GenBank® Accession No. ABM97856; GI No. 124264536), fluorescent protein SBFP2 (GenBank® Accession No. ABM97857, GI No. 124264538), EBFP2 (GenBank® Accession No. EF517318, GI No. 145666498), Azurite (Mena et al., *Nature Biotechnology*, 24:1569-1571 (2006)), mKalama1 (GenBank® Accession No. EF517317, GI No. 145666496), zinc finger protein 383 (GenBank® Accession No. EDU39924.1, GI No. 187972425), SEQ ID NO:445 set forth in U.S. Pat. No. 7,166,424 (GenBank® Accession No. ABN30727.1; GI No. 125148618), soluble-modified blue fluorescent protein (smBFP) (GenBank® Accession No. U70497.1; GI No. 1619752), polypeptides having the sequence set forth in GenBank® Accession No. CAE00365.1 (GI No. 32260521), polypeptides having the sequence set forth in GenBank® Accession No. CAE00361.1 (GI No. 32260509), polypeptides having the sequence set forth in GenBank® Accession No. CAE00361.1 (GI No. 32260509), ECFP polypeptides (GenBank® Accession No. AC048275.1; GI No. 226331138), Cerulean polypeptides (GenBank® Accession No. ADE48834.1; GI No. 293612838), Fluorescent Protein Cypet polypeptides (GenBank® Accession No. 3GEX_A; GI No. 290789997), MiCy polypeptides (GenBank® Accession No. ADE48830.1; GI No. 293612833), and mTFP1 fluorescent protein polypeptides (GenBank® Accession No. AC048263.1; GI No. 226320339). In some cases, a BFP polypeptide set forth in U.S. Patent Application Publication No. 2010/0062460 can be used as described herein.

Any appropriate RFP polypeptide and GFP polypeptide can be used as described herein. Examples of RFP polypeptides that can be used as described herein include, without limitation, soluble-modified red-shifted green fluorescent protein (smRSGFP) polypeptides (GenBank® Accession No. U70496.1; GI No. 1619750), red fluorescent protein polypeptides having the sequence set forth in GenBank® Accession No. AAG16224.1 (GI No. 10304307); AB038175.1 (GI No. 133753343); or AAU06852.1 (GI No. 51593130), Orange-Emitting Gfp-Like Protein polypeptides (GenBank® Accession No. 2ZMW_D; GI No. 209870302), mOrange fluorescent protein polypeptides (GenBank® Accession No. AC048285.1; GI No. 226331152), NLS-dTomato polypetides (GenBank® Accession No. ADC42843.1; GI No. 288188779), red fluorescent protein tdTomato polypeptides (GenBank® Accession No. ACQ43939.1; GI No. 228484713), DsRed polypeptides (GenBank® Accession No. BAE53441.1; GI No. 83016748), DsRed2 polypeptides (GenBank® Accession No. AAV73970.1; GI No. 56119204), DsRed-Express polypeptides (GenBank® Accession No. ACU30027.1; GI No. 255689290), DsRed-Monomer polypeptides (GenBank® Accession No. ACF35425.1; GI No. 194245628), monomeric orange-red fluorescent protein polypeptides (GenBank® Accession No. AAV52170.1; GI No. 55420625), monomeric orange-red fluorescent protein polypeptide (GenBank® Accession No. AAV52166.1; GI No. 55420617), mCherry polypeptides (GenBank® Accession No. ACY24904.1; GI No. 262089840), polypeptides having the amino acid sequence of SEQ ID NO:3 set forth in U.S. Pat. No. 7,393,923 (GenBank® Accession No. ACH06540.1; GI No. 197013979), and polypeptides having the amino acid sequence of SEQ ID NO:5 set forth in U.S. Pat. No. 7,393,923 (GenBank® Accession No. ACH06541.1; GI No. 197013980).

Examples of GFP polypeptides that can be used as described herein include, without limitation, soluble-modified green fluorescent protein (smGFP) polypeptides (GenBank® Accession No. U70495.1; GI No. 1619748), modified green fluorescent protein GFP-ER (mfgp4-ER) polypetpides (GenBank® Accession No. U87625.1; GI No. 1842446), GFP polypeptides (GenBank® Accession No. ACJ06700.1, GI No. 210076685), enhanced GFP polypeptides (GenBank® Accession No. ACV20892.1; GI No. 256708579), turboGFP polypeptides (GenBank® Accession No. ADD23343.1; GI No. 290131407), VisGreen GFP polypeptides (GenBank® Accession No. ABR26680.1; GI No. 149393496), and Azami-Green polypeptides (GenBank® Accession No. BAD52001.1; GI No. 52839539).

In some cases, a fluorescence emitting polypeptide such as those described by Subach et al. (*Chem. Biol.*, 15:1116-1124 (2008)) can be used as described herein. See, also, GenBank® Accession No. 3M24_A (GI No. 296863586), GenBank® Accession No. 3M24_B (GI:296863587), GenBank® Accession No. 3M24_C (GI:296863588), and GenBank® Accession No. 3M2_D (GI:296863589). Additional examples of fluorescence emitting polypeptides that can be used as described herein include, without limitation, those described elsewhere (Alieva et al. *PLoS ONE*, 3(7):e2680 (2008) and Chudafov et al., *Physiol. Rev.*, 90:1103-1163 (2010)). See, e.g., Table 1 of the Alieva et al. reference and FIGS. 5, 10, 12, and 14 of the Chudafov et al. reference. In some cases, a coral fluorescence emitting polypeptide can be used as described herein. In some cases, a fluorescence emitting polypeptide having the amino acid sequence set forth in FIG. 2 or 9 or having an amino acid sequence encoded by the sequence set forth in FIG. 1 can be used as described herein.

Any appropriate method can be used to make a fluorescence emitting polypeptide. For example, polypeptide expression techniques (e.g., heterologous expression techniques using bacterial cells, insect cells, or mammalian cells) can be used to make a fluorescence emitting polypeptide. In some cases, fluorescence emitting polypeptides such as BFP polypeptides can be made as described elsewhere (Yakhnin et al., *Protein Expr. Purif.*, 14:382-386 (1998) and Jain et al., *J. Chromatography A*, 1035:83-86 (2004)). In some cases, standard polypeptide synthesis techniques (e.g., liquid-phase polypeptide synthesis techniques or solid-phase polypeptide synthesis techniques) can be used to produce fluorescence emitting polypeptides synthetically.

A fluorescence emitting polypeptide can be attached or adhered to teeth via a molecule (e.g., a polypeptide) having the ability to interact with or bind to a tooth or a tooth component (e.g., enamel, hydroxyapatite, acquired dental pellicle, cementum, crown, cervix, cementoenamel junction, or apex). For example, a fluorescence emitting polypeptide can be covalently or non-covalently attached to a polypeptide (e.g., a casein polypeptide, a statherin polypeptide, or a fragment thereof). Examples of casein polypeptides that can be used as described herein include, without limitation, α-casein polypeptides (e.g., α-S1 casein polypeptides and α-S2 casein polypeptides), β-casein polypeptides (e.g., A1 β-casein polypeptides and A2 β-casein polypeptides), γ-casein polypeptides (e.g., γ1-casein polypeptides, γ2-casein polypeptides, and γ3-casein polypeptides), δ-casein polypeptides, and ε-casein polypeptides. In some cases, a casein polypeptide having the amino acid sequence set forth in FIG. 4 or 6 or having an amino acid sequence encoded by the sequence set forth in FIG. 3 or 5 can be used as described herein.

In some cases, a casein polypeptide can be a portion of a full length casein polypeptide provided that that portion has the ability to interact with or bind to a tooth or a tooth component. For example, a casein polypeptide that can be used as described herein can be a polypeptide that includes an anionic domain (e.g., amino acid residues 59 to 79 of a full length bovine α-S1 casein polypeptide, amino acid residues 2 to 20 of a full length bovine α-S2 casein polypeptide, or amino acid residues 1 to 25 of a full length bovine β casein polypeptide) of a casein polypeptide.

In some cases, a casein polypeptide can be (a) a polypeptide consisting of amino acid residues 59 through 79 of a full length bovine α-S1 casein polypeptide, (b) a polypeptide that is no more than 50 amino acid residues in length (e.g., no more than 45, 40, 35, 30, or 25 amino acid residues in length) provided that the polypeptide includes amino acid residues 59 through 79 of a full length bovine α-S1 casein polypeptide, or (c) a polypeptide that includes amino acid residues 59 through 79 of a full length bovine α-S1 casein polypeptide with zero, one, two, three, four, five, or six amino acid substitutions as compared to the amino acid residues 59 through 79 of a full length bovine α-S1 casein polypeptide. In some cases, a casein polypeptide can be (a) a polypeptide consisting of amino acid residues 1 through 25 of a full length bovine β casein polypeptide, (b) a polypeptide that is no more than 50 amino acid residues in length (e.g., no more than 45, 40, 35, or 30 amino acid residues in length) provided that the polypeptide includes amino acid residues 1 through 25 of a full length bovine β casein polypeptide, or (c) a polypeptide that includes amino acid residues 1 through 25 of a full length bovine β casein polypeptide with zero, one, two, three, four, five, or six amino acid substitutions as compared to the amino acid residues 1 through 25 of a full length bovine β casein polypeptide. In some cases, a casein polypeptide can be made (e.g., synthesized) to include one or more cysteine residues to facilitate conjugation of the casein polypeptide to a fluorescence emitting polypeptide (e.g., a BFP polypeptide).

A casein polypeptide that can be used as described herein can have an amino acid sequence that is naturally occurring in any type of mammal. For example, a casein polypeptide that can be used as described herein can have an amino acid sequence that is naturally occurring in a human, cow, goat, sheep, horse, mouse, rat, monkey, dog, cat, orangutan, chimp, pig, horse, elephant, or opossum. In some cases, a bovine casein polypeptide is conjugated to a fluorescence emitting polypeptide to form a casein polypeptide/fluorescence emitting polypeptide conjugate having the ability to interact with or bind to a tooth or a tooth component.

Examples of statherin polypeptides that can be used as described herein include, without limitation, human statherin polypeptides, bovine statherin polypeptides, and salivary statherin polypeptides. In some cases, a statherin polypeptide can be a portion of a full length statherin polypeptide provided that that portion has the ability to interact with or bind to a tooth or a tooth component. For example, a statherin polypeptide that can be used as described herein can be a polypeptide that includes a highly negative domain (e.g., amino acid residues 1 to 15 of a full length human statherin polypeptide) of a statherin polypeptide.

In some cases, a statherin polypeptide can be (a) a polypeptide consisting of amino acid residues 1 through 15 of a full length human statherin polypeptide, (b) a polypeptide that is no more than 50 amino acid residues in length (e.g., no more than 45, 40, 35, 30, 25, or 20 amino acid residues in length) provided that the polypeptide includes amino acid residues 1 through 15 of a full length human statherin polypeptide, or (c) a polypeptide that includes amino acid residues 1 through 15 of a full length human statherin polypeptide with zero, one, two, three, four, or five amino acid substitutions as compared to the amino acid residues 1 through 15 of a full length human statherin polypeptide. In some cases, a statherin polypeptide can be (a) a polypeptide consisting of amino acid residues 1 through 25 of a full length human statherin polypeptide, (b) a polypeptide that is no more than 50 amino acid residues in length (e.g., no more than 45, 40, 35, or 30 amino acid residues in length) provided that the polypeptide includes amino acid residues 1 through 25 of a full length human statherin polypeptide, or (c) a polypeptide that includes amino acid residues 1 through 25 of a full length human statherin polypeptide with zero, one, two, three, four, five, or six amino acid substitutions as compared to the amino acid residues 1 through 25 of a full length human statherin polypeptide. In some cases, a statherin polypeptide can be (a) a polypeptide consisting of amino acid residues 19 through 43 of a full length human statherin polypeptide, (b) a polypeptide that is no more than 50 amino acid residues in length (e.g., no more than 45, 40, 35, 30, or 25 amino acid residues in length) provided that the polypeptide includes amino acid residues 19 through 43 of a full length human statherin polypeptide, or (c) a polypeptide that includes amino acid residues 19 through 43 of a full length human statherin polypeptide with zero, one, two, three, four, five, or six amino acid substitutions as compared to the amino acid residues 19 through 43 of a full length human statherin polypeptide. In some cases, a statherin polypeptide can be made (e.g., synthesized) with a negative residue (e.g., an aspartic acid) substituted for one or more negative phosphoserine residues. In some cases, a statherin polypeptide can be made (e.g., synthesized) to include one or more cysteine residues to facilitate conjugation of the statherin polypeptide to a fluorescence emitting polypeptide (e.g., a BFP polypeptide).

A statherin polypeptide that can be used as described herein can have an amino acid sequence that is naturally occurring in any type of mammal. For example, a statherin polypeptide that can be used as described herein can have an amino acid sequence that is naturally occurring in a human, cow, goat, sheep, horse, mouse, rat, monkey, dog, cat, orangutan, chimp, pig, horse, elephant, or opossum. In some cases, a human statherin polypeptide is conjugated to a fluorescence emitting polypeptide to form a statherin polypeptide/fluorescence emitting polypeptide conjugate having the ability to interact with or bind to a tooth or a tooth component. In some cases, a statherin polypeptide having the amino acid sequence set forth in FIG. 8 or having an amino acid sequence encoded by the sequence set forth in FIG. 7 can be used as described herein.

Any appropriate method can be used to make a polypeptide having the ability to interact with or bind to a tooth or a tooth component. For example, polypeptide expression techniques (e.g., heterologous expression techniques using bacterial cells, insect cells, or mammalian cells) can be used to make a polypeptide having the ability to interact with or bind to a tooth or a tooth component. In some cases, a polypeptide having the ability to interact with or bind to a tooth or a tooth component such as a casein polypeptide or a statherin polypeptide can be made as described elsewhere (U.S. Pat. Nos. 7,666,996, 6,797,810, 6,558,717, 6,121,421, 6,080,844, 5,834,427, 5,391,497, and 4,713,254, and U.S. Patent Application Publication Nos. 2009/0074680 and 2010/0144598). In some cases, standard polypeptide synthesis techniques (e.g., liquid-phase polypeptide synthesis techniques or solid-phase polypeptide synthesis techniques) can be used to produce synthetically polypeptides having the ability to interact with or bind to a tooth or a tooth component.

Any appropriate method can be used to covalently or non-covalently attach a fluorescence emitting polypeptide to a molecule (e.g., a polypeptide) having the ability to interact with or bind to a tooth or a tooth component. For example, a fluorescence emitting polypeptide such as a BFP polypeptide can be chemically conjugated to a casein polypeptide and/or a statherin polypeptide via one or more coordinate covalent bonds, covalent bonds, disulfide bonds, high energy bonds, hydrogen bonds, ionic bonds, or peptide bonds. In some cases, a fluorescence emitting polypeptide can be chemically conjugated to an amine group present on a polypeptide having the ability to interact with or bind to a tooth or a tooth component (e.g., a casein polypeptide and/or a statherin polypeptide). Such an amine group can be located at the N-terminus of the polypeptide, the C-terminus of the polypeptide, or in between the N- and C-termini of the polypeptide.

In some cases, the polypeptides to be conjugated can be activated prior to conjugation. For example, a polypeptide (e.g., a casein polypeptide or a statherin polypeptide) can be activated by incorporation of a reactive thiol group. For a statherin polypeptide, for example, this can be accomplished by adding a cysteine residue to the polypeptide during chemical synthesis. For a casein polypeptide, a casein polypeptide can be thiolated by reaction with 2-iminothiolane (e.g., a Traut's reagent) as described elsewhere (McCall et al., *Bioconjugate Chem.*, 1:222-226 (1990)). In the cases of α- and β-casein polypeptides, there can be multiple amines (e.g., the N-terminus and lysines) on the polypeptide that can react with Traut's reagent. The reaction conditions can be varied to maximize the yield of molecules activated with one or two thiols to decrease the possibility that conjugation may interfere with teeth binding. The degree of thiol incorporation can be measured using a sensitive fluorescence assay as described elsewhere (Lacy et al., *Analytical Biochemistry*, 382:66-68 (2008)).

A fluorescence emitting polypeptide can be substituted with one or more maleimide groups via reaction of the polypeptide's amines with a bifunctional reagent containing a maleimide group and a reactive N-hydroxysuccinimide ester. The maleimide substituted fluorescence emitting polypeptide can then be conjugated to the thiol groups of the polypeptide having the ability to interact with or bind to a tooth or a tooth component. The degree to which the fluorescence emitting polypeptide is substituted with maleimide groups can be varied as described elsewhere (Singh, *Bioconjugate Chem.*, 5:348-351 (1994)).

Additional examples of conjugation methods that can be used to conjugate a fluorescence emitting polypeptide to a molecule (e.g., a polypeptide) having the ability to interact with or bind to a tooth or a tooth component include, without limitation, those described in elsewhere (e.g., Hermanson, G. T. Bioconjugate Techniques, Second Edition, 2008, Elsevier). See, e.g., Part I, Section 4 and Part II, Section 5.

In some cases, the fluorescent signal that is obtained using the methods and materials provided herein can be enhanced by linking multiple fluorescence emitting polypeptides to a single molecule (e.g., a polypeptide) having the ability to interact with or bind to a tooth or a tooth component. Because of steric effects, this amplification can be effectively accomplished by first preparing a polymer containing multiple fluorescence emitting polypeptides and then linking this polymer to a molecule (e.g., a casein polypeptide) having the ability to interact with or bind to a tooth or a tooth component. Examples of methods (e.g., polymerization methods) that can be used to form polymers containing multiple fluorescence emitting polypeptides include, without limitation, those described elsewhere (e.g., Hermanson, G. T. Bioconjugate Techniques, Second Edition, 2008, Elsevier). See, e.g., Part II, Section 25.

In some cases, a fluorescence emitting polypeptide can be produced as a fusion or chimeric polypeptide with a polypeptide having the ability to interact with or bind to a tooth or a tooth component. For example, heterologous polypeptide expression techniques or synthetic polypeptide synthesis techniques can be used to produce a single polypeptide chain having an amino acid sequence of a fluorescence emitting polypeptide and an amino acid sequence of a polypeptide having the ability to interact with or bind to a tooth or a tooth component. In some cases, the single polypeptide chain can have (a) an amino acid sequence of a fluorescence emitting polypeptide followed by an amino acid sequence of a polypeptide having the ability to interact with or bind to a tooth or a tooth component or (b) an amino acid sequence of a polypeptide having the ability to interact with or bind to a tooth or a tooth component followed by an amino acid sequence of a fluorescence emitting polypeptide. In some cases, the single polypeptide chain can have one or more (e.g., one, two, three, four, or five) amino acid sequences with each encoding a fluorescence emitting polypeptide and one or more (e.g., one, two, three, four, or five) amino acid sequences with each encoding a polypeptide having the ability to interact with or bind to a tooth or a tooth component.

In some cases, a fusion or chimeric polypeptide provided herein can include other amino acid sequences (e.g., spacers or binding residues). For example, a fusion or chimeric polypeptide having an amino acid sequence of a fluorescence emitting polypeptide and an amino acid sequence of a polypeptide having the ability to interact with or bind to a tooth or a tooth component can include one or more additional amino acid residues such as glycine, lysine, alanine, arginine, asparagine, aspartic acid, cysteine, glutamine acid, glutamine, isoleucine, leucine, methionine, phenylalanine, threonine, tryptophan, proline, histidine, valine serine, tyrosine, ornithine, taurine, pyrolysine, or seleocysteine residues, or amino acid derivatives (e.g., 5-hydroxytryptophan, L-dihydroxyphenylalanine, or α-difluoromethylornithine). Such additional amino acid residues can be designed to be spacers (e.g., a string of five or more glycine residues) or can be designed to allow polypeptides or other molecules to be chemically conjugated to the fusion or chimeric polypeptide. For example, a fusion or chimeric polypeptide having an amino acid sequence of a fluorescence emitting polypeptide and an amino acid sequence of a polypeptide having the ability to interact with or bind to a tooth or a tooth component can include one, two, three, four, five, or more additional lysine residues such that one or more polypeptides having the ability to interact with or bind to a tooth or a tooth component (e.g., casein polypeptides and/or statherin polypeptides) can be chemically conjugated to the fusion or chimeric polypeptide.

A composition provided herein containing a fluorescence emitting polypeptide (e.g., a composition containing a fluorescence emitting polypeptide, a fluorescence emitting polypeptide/casein polypeptide conjugate, a fluorescence emitting polypeptide/statherin polypeptide conjugate, a fluorescence emitting polypeptide/casein polypeptide fusion polypeptide, and/or a fluorescence emitting polypeptide/statherin polypeptide fusion polypeptide) can be applied to teeth to alter the appearance of the teeth. For example, a composition provided herein containing a BFP polypeptide (e.g., a BFP polypeptide/statherin polypeptide conjugate) can be applied to teeth to give the teeth a whiter appearance. Any appropriate method can be used to deliver a composition provided herein to teeth. For example, a composition provided herein can be incorporated into a tooth paste, a mouth wash, a drink, a food product, gum, gels, powders, or creams.

In some cases, an effective amount of a composition provided herein can be delivered to teeth such that the appearance of the teeth is altered (e.g., the appearance of the teeth becomes whiter). An effective amount of a composition provided herein can be any amount that alters the appearance of teeth without inducing significant toxicity. For example, a composition provided herein can be incorporated into a tooth paste product in an amount that results in between about 0.0001 mg and about 100 mg (e.g., between about 0.001 mg and about 100 mg, between about 0.01 mg and about 100 mg, between about 0.1 mg and about 100 mg, between about 0.5 mg and about 100 mg, between about 0.5 mg and about 50 mg, between about 0.5 mg and about 25 mg, between about 1 mg and about 100 mg, between about 1 mg and about 50 mg, or between about 1 mg and about 25 mg) of fluorescence emitting polypeptide per gram of tooth paste.

In some cases, a composition provided herein can be applied to teeth for a period of time prior to washing, swallowing, or removal such that the appearance of the teeth is altered (e.g., the appearance of the teeth becomes whiter). For example, a tooth paste configured to include a fluorescence emitting polypeptide as described herein can be applied to teeth and remain in contact with those teeth, without rinsing, for between 30 seconds and 10 minutes (e.g., between 30 seconds and 5 minutes, between 30 seconds and 2.5 minutes, between 30 seconds and two minutes, between 1 minute and 10 minutes, between 2 minutes and 10 minutes, or between one minute and 5 minutes).

In some cases, a person's teeth can be prepared prior to delivering a composition provided herein. For example, a person's teeth can be washed, brushed, or polished (e.g., polished with pumice) prior to delivering a composition provided herein. In some cases, the surface of the tooth or teeth to be treated can be treated with one or more agents capable of exposing calcium phosphate binding sites. For example, teeth to be treated with a composition provided herein can be contacted with EDTA or phosphoric acid to expose calcium phosphate binding sites present on the teeth. In the case of phosphoric acid treatment, only the tooth enamel can be exposed to the acid to prevent or reduce the risk of soft tissue damage.

In some cases, a two or more step process can be used to apply a fluorescence emitting polypeptide to teeth. For example, a composition containing a molecule (e.g., a polypeptide) having the ability to interact with or bind to a tooth or a tooth component can be delivered to the teeth to be treated as one step followed by a step of delivering a fluorescence emitting polypeptide having the ability to interact with or bind to the delivered molecule. In some case, these two steps can be performed at the same time using a single composition that contains the molecule separate from the fluorescence emitting polypeptide or using separate compositions where one composition contains the molecule and another composition contains the fluorescence emitting polypeptide.

In some cases, an assay can be performed to confirm that a composition provided herein or a component of a composition provided herein (e.g., a casein polypeptide) has binding affinity for teeth or a tooth component. For example, a material to be tested can be incubated with a hydroxyapatite (HA) matrix and the amount of material in solution after HA binding can be compared with the initial concentration to determine, by difference, the amount of bound material. See, e.g., Raj et al., *J. Biol. Chem.*, 267:5968-5976 (1992). In some cases, the HA bound material can be directly measured after dissolving the HA matrix with EDTA (Lamkin et al., *J. Dent. Res.*, 75:803-808 (1996)). In the case of a polypeptide material, the polypeptide concentration in solution can be measured using a bicinchoninic acid assay and/or an ortho-phthalaldehyde amine assay. Binding constants can be determined using the Langmuir Model (Bouropoulos and Moradian-Oldak, *Calcif. Tissue Int.*, 72:599-603 (2003)). In some case, an assay can be performed with an HA matrix that was pre-incubated with human saliva to coat the HA with proteins as described elsewhere (Lamkin et al., *J. Dent. Res.*, 75:803-808 (1996)). In such cases, unbound saliva proteins can be removed by washing since their presence may interfere with the polypeptide concentration determinations.

Any appropriate method can be used to assess the affinity of a composition provided herein for teeth or an HA matrix. For example, bound and unbound compositions can be quantified by measuring the fluorescence of the fluorescence emitting polypeptide of the composition. The ability to utilize fluorescence for quantification can allow for one to measure the binding of the composition to HA in the presence of human saliva. In some cases, a composition provided herein can be assessed for the ability to bind in vitro to human teeth. The teeth can be subjected to different degrees of cleaning, such as brushing or polishing with pumice. The teeth can then be treated with human saliva to form the acquired dental pellicle and incubated with a composition provided herein in the presence and absence of saliva. The binding to teeth can be determined both by measuring the bound and unbound fluorescence. The extraction of bound fluorescence emitting polypeptides from teeth can be completed using gentle procedures. For example, teeth can be swabbed with filter paper collection strips, and the polypeptides can be extracted from the paper under mild conditions as described elsewhere (Siqueira and Oppenheim, *Archives of Oral Biology*, 54:437-444 (2009)). In some cases, the teeth can be analyzed by fluorescence microscopy to assess the relative amount of fluorescence emitting polypeptide bound under different conditions.

Any appropriate method can be used to assess a composition provided herein for the ability to alter the appearance of teeth. For example, visual inspection techniques can be used to determine whether or not a composition provided herein can alter the appearance of teeth. Such visual inspection techniques can include using shade guides for comparison as described elsewhere (Paravina et al., *J. Esthet. Restor. Dent.*, 19:276-283 (2007)). In some cases, the ability of a composition provided herein to alter the appearance of teeth (e.g., to make teeth appear whiter) can be measured using reflectance spectrophotometry. In such cases, the teeth can be illuminated with a white light source and analyzed as to the amount of light absorbed at different wavelengths by reflectance spectrophotometry (colorimetry). These measurements can then be repeated with the UV light filtered from the light source. The difference in the reflectance values obtained with the inclusion and exclusion of UV light is the UV fluorescence spectrum of the tooth surface (see, e.g., Park et al., *M. Dental Materials*, 23:731-735 (2007)).

A composition provided herein can have a low risk of toxicity to the person using the composition, can contain one or more polypeptides of human origin, can contain one or more polypeptides naturally present in food or drink products, and/or can lack potentially toxic dyes.

The invention will be further described in the following examples, which do not limit the scope of the invention described in the claims.

EXAMPLES

Example 1

Methods for Obtaining Casein Polypeptide Mixtures

Casein, α-casein, and β-casein were reacted with trypsin to produce the respective casein phosphopeptides (casein-PP, α-casein-PP, and β-casein-PP). The trypsin and the three caseins were purchased from Sigma-Aldrich. The methods used in these preparations were adapted from those described elsewhere (Reynolds et al., *Anal. Biochem.*, 217:277-284 (1994)). Briefly, hydrolysis of casein, α-casein, and β-casein polypeptides were performed in 3 mL reactions that contained 60 mg of polypeptide, 0.05 M Tris buffer (pH 8), and either 1.2 mg, 0.6 mg, or 0.3 mg of trypsin. The reactions were allowed to proceed overnight at room temperature (21° C.) at which time the pH of the reaction mixtures were adjusted to pH 4.6 with 1 M hydrochloric acid. Any precipitate at this stage was removed by centrifugation (12,000×g for 15 minutes). A 10% calcium chloride solution in water was then added to adjust the calcium concentration to 1%, and polypeptides that contained multiple phosphoserine groups were precipitated by addition of an equal volume of 100% ethanol. The precipitated polypeptides were collected by centrifugation (12,000×g for 15 minutes). The precipitates were redissolved in 0.5 mL of phosphate buffered saline for analysis.

The polypeptide concentration in the precipitates was determined by bicinchoninic acid assay using the reagents and protocol in the Pierce BCA Assay Kit. The sizes and relative concentrations of the polypeptides after trypsin hydrolysis were determined by sodium dodecylsulfate polyacrylamide gel electrophoresis (SDS-PAGE) using 16.5% Tricine gels (BioRad). Samples (10 μL) were mixed with an equal volume of Tricine Sample Buffer (BioRad) and heated at 95° C. for 5 minutes prior to being loaded onto a gel and electrophoresed for 100 minutes at 100 volts (constant) at room temperature. The gels were fixed by gently shaking them for 1 hour at room temperature in a solution of 40% methanol/10% acetic acid and then stained by incubation for 30 minutes at room temperature in a solution of 50% Coomassie Brilliant Blue (BioRad) and 50% of the fix solution. Finally, the gels were destained by gently shaking overnight in 1% acetic acid.

Casein was hydrolyzed at pH 8 in three mL reactions that contained 60 mg of casein and 1.2 mg, 0.6 mg, and 0.3 mg of trypsin. The percentage of the polypeptides produced by the hydrolysis reactions that were recovered by the precipitation procedure were 9%, 9%, and 13% for the reactions containing 1.2 mg, 0.6 mg, and 0.3 mg of trypsin, respectively. SDS-PAGE analysis indicated that, in all cases, the casein was hydrolyzed to a mixture of smaller polypeptides. After precipitation, the recovered material from all three reactions was mainly small molecular weight polypeptides.

α-Casein and β-casein were hydrolyzed in three mL reactions at pH 8 that contained 60 mg of polypeptides and 1.2 mg of trypsin. The calcium chloride/ethanol precipitates for α-casein and β-casein contained 4% and 7% of the hydrolyzed polypeptides, respectively. SDS-PAGE analysis indicated that the precipitated samples contain polypeptide mixtures.

Example 2

Forming Conjugates of BFP Polypeptides and Molecules Having the Ability to Interact with or Bind to a Tooth Component Unlabeled β-casein (Sigma-Aldrich), β-casein-phosphopeptides (produced according to Example 1), and statherin(1-25)-C (Biomatic) were conjugated to BFP polypeptides obtained from Biovision to form β-casein/BFP conjugates, β-casein-PP/BFP conjugates, and statherin(1-25)C/BFP conjugates, respectively. This example describes the conjugation of β-casein, but the conjugation of α-casein and β-casein phosphopeptides was performed using similar procedures. Briefly, maleimide activated BFP was prepared in a 3 mL reaction that contained 1 mg/mL BFP, 0.33 mg/mL SM(PEG)$_4$ (Pierce, cat #22104), 2 mM EDTA, 0.05% Tween 20, and 0.05 M sodium phosphate buffer (pH 7.2). The reaction was allowed to proceed for 40 minutes at room temperature and then desalted on a G-25 Sephadex column equilibrated in 5 mM MES buffer (pH 6), 2 mM EDTA, and 0.05% Tween 20.

Thiol activated β-casein was prepared in a 2 mL reaction that contained 4.5 mg/mL β-casein, 5 mM 2-iminothiolane, 2 mM EDTA, 0.05% Tween 20, and 0.05 M sodium borate buffer (pH 8.0). The reaction was allowed to proceed for 1 hour at room temperature and then desalted on a G-25 Sephadex column equilibrated in 0.05 M sodium phosphate buffer (pH 7.0), 2 mM EDTA, and 0.05% Tween 20. This material was used in the conjugation reaction immediately after preparation.

The β-casein/BFP conjugate was prepared in a 3.825 mL reaction that contained 0.37 mg/mL maleimide activated BFP, 1.57 mg/mL thiol activated β-casein, 2 mM EDTA, 0.05% Tween 20, and 0.05 M sodium phosphate buffer (pH 7.0). The reaction was allowed to proceed for 1 hour at room temperature and then any remaining thiols were quenched by the addition of 0.038 mL of a freshly prepared solution of 0.1 M N-methylmaleimide in deionized water.

The conjugate was concentrated to 1.5 mL via a centrifugal concentrator (10 kDa cutoff) and then applied to a HiLoad Superdex 200 16/600 column (GE Healthcare) equilibrated in phosphate buffered saline containing 0.05% Tween 20. The column was eluted at 1.1 mL/minute, and 1.5 mL fractions were collected and analyzed both by fluorescence (320 nm excitation, 445 nm emission) and total protein concentration (bincinchoninic acid assay).

Because both β-casein and BFP contain multiple activating groups, various sized conjugates were formed in the reaction. Examples of different sized conjugates are β-casein-BFP; β-casein-BFP-β-casein; β-casein-BFP-β-casein-BFP, etc. The Superdex 200 column separated the smaller starting materials from the conjugates based on molecular size. The column also, however, partially separated the different sized conjugates produced in the reaction. The column products were collected in two pools: the higher molecular weight products that eluted first from the column and the lower molecular weight products that eluted after the higher molecular weight products but before the unreacted starting materials. After the two product pools were concentrated by molecular filtration, the lower molecular weight pool (0.28 mg/mL BFP content) exhibited greater binding to teeth than the higher molecular weight pool (0.36 mg/mL BFP content). The higher binding low molecular weight fraction was used in the examples shown below.

β-Casein phosphopeptide was thiolated, coupled to maleimide activated BFP, purified on a Superdex 200 column, and concentrated as described for β-casein. The higher molecular weight fraction of the β-casein phosphopeptide-BFP had a concentration of 0.38 mg/mL, and the lower molecular weight fraction had a concentration of 0.48 mg/mL.

A typical statherin(1-25)C/BFP conjugate was prepared in a 1.4 mL reaction that contained 1.1 mg/mL maleimide activated BFP, 1.1 mg/mL statherin(1-25)C, 2 mM EDTA, 0.05% Tween 20, and 0.05 M sodium phosphate buffer (pH 7.0). The statherin(1-25)C contained a free thiol and didn't require activation. Although there is only one active group per statherin molecule, multiple statherin molecules can attach to a single activated BFP, creating a product distribution. The products were partially separated from each other on the Superdex 200 column resulting in a higher molecular weight fraction (0.22 mg/mL BFP content) and a lower molecular weight fraction (036 mg/mL BFP content). The higher molecular weight fraction was used in the binding/extraction example shown below.

Example 3

Applying BFP Polypeptide-Containing Conjugates to Teeth

β-casein/BFP conjugates (about 0.09 mg/mL), β-casein-PP/BFP conjugates (about 0.24 mg/mL), and statherin(1-25) C/BFP conjugates (about 0.05 mg/mL) were incubated with uncoated teeth or saliva-coated teeth for about one hour. After the one-hour incubation, the teeth were washed, and the bound proteins were extracted from the teeth with 0.4 percent EDTA followed by 2 percent SDS. The amount of extracted protein in each extraction solvent was determined via a fluorescent assay (Table 1).

TABLE 1

| | | BFP-Conjugate Extracted from Teeth | | |
| --- | --- | --- | --- | --- |
| Samples | Sample Concentration mg/mL | 0.4% EDTA Extraction µg | 2% SDS Extraction µg | Total BFP-Conjugate Extracted µg |
| Uncoated Teeth | | | | |
| β-Casein-BFP | 0.09 | 0.25 | 0.42 | 0.67 |
| β-Casein-PP | 0.24 | 0.20 | 0.14 | 0.34 |
| Statherin(1-25)Cys-BFP | 0.05 | 0.40 | 0.18 | 0.58 |
| Control | — | 0.01 | <0.01 | <0.02 |
| Saliva Coated Teeth | | | | |
| β-Casein-BFP | 0.09 | 0.14 | 0.10 | 0.24 |
| β-Casein-PP | 0.24 | 0.14 | 0.16 | 0.3 |
| Statherin(1-25)Cys-BFP | 0.05 | 0.10 | 0.13 | 0.23 |
| Control | — | <0.02 | 0.05 | <0.07 |

These results demonstrate that β-casein/BFP conjugates, β-casein-PP/BFP conjugates, and statherin(1-25)C/BFP conjugates have the ability to bind to teeth.

Additional experiments were performed using β-casein/BFP conjugates to assess the effects of pH and temperature on binding. There was no significant change in binding of β-casein/BFP conjugates to teeth from pH 6 to pH 9. In addition, there was no significant effect of temperature (21° C. to 37° C.) on binding of β-casein/BFP conjugates to teeth.

In another experiment, β-casein/BFP conjugates were incubated with teeth in the presence of 40 percent ethanol. In some cases, a buffer containing 40 percent ethanol was found to increase the level of binding of β-casein/BFP conjugates to teeth as compared to the use of β-casein/BFP conjugates in the absence of ethanol.

Pre-treatment of teeth with 2 percent EDTA for one hour resulted in an increase in the level of binding of β-casein/BFP conjugates and statherin (1-25)C/BFP conjugates to teeth.

The following was performed to assess teeth whitening. Briefly, pumiced teeth were incubated with 2 percent SDS for 30 minutes followed by an incubation with 50 percent ethanol for 10 minutes. After the 10-minute incubation with 50 percent ethanol, the teeth were exposed to a binding buffer containing saliva salts for 30 minutes and then incubated with 2 percent EDTA for one hour. After the one hour incubation with EDTA, the teeth were exposed to the BFP-containing conjugate for one hour and then washed. Bound conjugate was extracted with 2 percent SDS for 30 minutes at 37° C. and measured. At this point, the teeth were pumiced and optionally re-used in a subsequent experiment. Samples were generally analyzed for whitening (a) after EDTA treatment and before conjugate binding, (b) after the one-hour conjugate binding step, (c) after the SDS extraction step, and (d) after pumicing. At each of these steps, the teeth were analyzed using a shade guide analysis, fluorescence imaging, and/or photography (e.g., a fixed camera setting, lighting (6500° K. Bulbs), and sample placement). The SDS extract samples were analyzed for fluorescence.

β-casein/BFP conjugates in the presence of buffer containing 40 percent ethanol reproducibly whitened teeth as determined by both shade guide analysis and photographic comparisons (FIG. 10). β-casein/BFP conjugates in the presence of buffer alone were assessed using the shade guide analysis and found to whiten teeth. Statherin(1-25)C/BFP conjugates in the presence of 40 percent ethanol whitened teeth as determined by both shade guide analysis and photographic comparisons. The level of whitening was less than that of the β-casein/BFP conjugates. Statherin(1-25)C/BFP conjugates in the presence buffer alone exhibited little or no whitening based on shade guide and photographic analyses.

In some cases, the whitening measurements that confirmed the ability of the conjugates to whiten teeth were performed after the teeth were washed with buffer. These results indicate that the bound conjugate was not easily removed. After pumicing, the teeth lost their whitening. Prior to pumicing, however, the teeth were washed with buffer and extracted with SDS to remove the conjugate. After this SDS treatment, the teeth were just marginally less white than they were before the buffer wash and SDS extraction. These results also indicate that the bound conjugate was not easily removed.

Taken together, the results provided herein demonstrate that conjugates such as β-casein/BFP polypeptide conjugates have the ability to bind to teeth and to make them appear modestly whiter.

Example 4

Applying a Composition Containing BFP Polypeptides to Human Teeth

A standard tooth paste composition is used to clean a human's teeth using standard brushing techniques. Once the teeth are cleaned, the human self-applies a paste composition containing BFP polypeptides to the cleaned teeth. Once applied, the composition containing BFP polypeptides is allowed to remain in contact with the teeth for at least 30 seconds (e.g., between about 30 seconds and 60 minutes). After this time period, the teeth are rinsed.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making teeth appear whiter, wherein said method comprises applying, to teeth, a conjugate comprising multiple blue fluorescent protein (BFP) polypeptides linked to a polypeptide having the ability to interact with or bind to a tooth or a tooth component, wherein fluorescence emitted from said BFP polypeptides makes said teeth appear whiter.

2. The method of claim 1, wherein said teeth are human teeth.

3. The method of claim 1, wherein said polypeptide is a polypeptide having the ability to bind to a tooth.

4. The method of claim 1, wherein said polypeptide is a polypeptide having the ability to bind to a tooth component.

5. The method of claim 1, wherein said polypeptide is a casein polypeptide.

6. The method of claim 1, wherein said polypeptide is a statherin polypeptide.

7. The method of claim 1, wherein a BFP polypeptide of said BFP polypeptides is linked to said polypeptide via a thiol group.

8. The method of claim 1, wherein said conjugate is present within tooth paste, and said applying step comprises applying said tooth paste to said teeth.

* * * * *